(12) United States Patent
Keleny et al.

(10) Patent No.: US 11,925,573 B2
(45) Date of Patent: *Mar. 12, 2024

(54) ENCLOSURE VENTILATION FILTER AND ASSEMBLY METHOD

(71) Applicant: Donaldson Company, Inc., Bloomington, MN (US)

(72) Inventors: Lloyd G. Keleny, Champlin, MN (US); Veli E. Kalayci, Farmington, MN (US); Michael J. Hebert, St. Paul, MN (US); Yehya A. Elsayed, St. Paul, MN (US); David W. Mulder, Bloomington, MN (US); Andrew J. Dallas, Lakeville, MN (US)

(73) Assignee: Donaldson Company, Inc., Bloomington, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/087,394

(22) Filed: Dec. 22, 2022

(65) Prior Publication Data

US 2023/0225896 A1 Jul. 20, 2023

Related U.S. Application Data

(60) Continuation of application No. 16/870,578, filed on May 8, 2020, now Pat. No. 11,534,324, which is a
(Continued)

(51) Int. Cl.
*A61F 5/445* (2006.01)
*A61F 5/441* (2006.01)
(Continued)

(52) U.S. Cl.
CPC .......... *A61F 5/441* (2013.01); *A61F 13/0008* (2013.01); *B01D 39/00* (2013.01);
(Continued)

(58) Field of Classification Search
CPC ..... A61F 5/445; A61F 13/0008; B01D 39/00; B01D 46/00; B01D 2253/00; B01D 69/147
See application file for complete search history.

(56) References Cited

U.S. PATENT DOCUMENTS

| 3,952,727 A | * | 4/1976 | Nolan | A61F 5/441 600/32 |
| 4,120,715 A | * | 10/1978 | Ockwell | B32B 3/266 156/289 |

(Continued)

FOREIGN PATENT DOCUMENTS

| EP | 0235928 A1 | 9/1987 |
| EP | 0358316 | 3/1990 |

(Continued)

OTHER PUBLICATIONS

"Communication of Notice of Opposition," for European Patent Application No. 09755439.8 dated Oct. 20, 2016 (29 pages).
(Continued)

*Primary Examiner* — Guy K Townsend
(74) *Attorney, Agent, or Firm* — Pauly, DeVries Smith & Deffner LLC

(57) ABSTRACT

A filter assembly for an enclosure, particularly for an ostomy bag, is described having an enclosure side, a first layer which is gas permeable, and an adsorbent layer comprising adsorbent particles dispersed in a fine fiber web. The enclosure side of the filter assembly includes an adhesive zone in which adhesive is present having an outer adhesive perimeter and a weld area surrounding at least a portion of the adhesive zone, where the filter assembly is heat-sealable to the enclosure at the weld area. A method of assembly is also described.

20 Claims, 11 Drawing Sheets

Related U.S. Application Data division of application No. 14/624,202, filed on Feb. 17, 2015, now Pat. No. 10,646,370, which is a continuation of application No. 12/414,951, filed on Mar. 31, 2009, now Pat. No. 8,979,811.

(60) Provisional application No. 61/041,244, filed on Apr. 1, 2008.

(51) Int. Cl.
*A61F 13/00* (2006.01)
*B01D 39/00* (2006.01)
*B01D 46/00* (2022.01)
*B01D 69/14* (2006.01)

(52) U.S. Cl.
CPC ............ *B01D 46/00* (2013.01); *B01D 69/147* (2013.01); *B01D 2253/00* (2013.01)

(56) References Cited

U.S. PATENT DOCUMENTS

| | | | |
|---|---|---|---|
| 4,203,445 A * | 5/1980 | Jessup | A61F 5/441 604/333 |
| 4,274,848 A | 6/1981 | La Gro | |
| 4,318,406 A | 3/1982 | McLeod | |
| 4,372,308 A * | 2/1983 | Steer | A61F 5/441 604/333 |
| 4,395,332 A * | 7/1983 | Klein | C02F 1/288 210/502.1 |
| 4,460,392 A | 7/1984 | Poulsen et al. | |
| 4,490,145 A * | 12/1984 | Campbell | A61F 5/441 604/333 |
| 4,668,258 A * | 5/1987 | Steer | B32B 27/065 96/135 |
| 4,723,951 A | 2/1988 | Steer | |
| 4,917,689 A * | 4/1990 | Coombes | A61F 5/445 604/338 |
| 4,957,522 A | 9/1990 | Brassell | |
| 5,074,851 A | 12/1991 | Plass et al. | |
| 5,085,652 A * | 2/1992 | Johnsen | A61B 17/32053 604/339 |
| 5,207,970 A | 5/1993 | Joseph et al. | |
| 5,250,042 A * | 10/1993 | Torgalkar | A61F 5/441 604/339 |
| 5,304,157 A | 4/1994 | Brooks et al. | |
| 5,306,264 A | 4/1994 | Ferguson et al. | |
| 5,417,678 A * | 5/1995 | Baumann | A61F 5/441 604/333 |
| 5,549,587 A | 8/1996 | Norton | |
| 5,591,144 A | 1/1997 | Shelley et al. | |
| 5,643,234 A * | 7/1997 | Lesko | A61F 5/441 604/338 |
| 5,690,622 A | 11/1997 | Smith et al. | |
| 5,952,422 A | 9/1999 | Chang et al. | |
| 6,120,536 A | 9/2000 | Ding et al. | |
| 6,129,716 A * | 10/2000 | Steer | A61F 5/441 604/338 |
| 6,135,986 A * | 10/2000 | Leisner | A61F 5/441 604/324 |
| 6,241,712 B1 * | 6/2001 | Steer | A61F 5/441 604/333 |
| 6,359,100 B1 | 3/2002 | Hostettler et al. | |
| 6,506,184 B1 * | 1/2003 | Villefrance | A61F 5/441 604/333 |
| 6,659,988 B1 * | 12/2003 | Steer | A61F 5/441 604/335 |
| 6,695,826 B2 | 2/2004 | Villefrance | |
| 6,723,428 B1 * | 4/2004 | Foss | B32B 27/306 428/324 |
| 6,773,420 B2 * | 8/2004 | Kanbara | A61F 5/441 604/333 |
| 6,946,196 B2 * | 9/2005 | Foss | B01D 46/521 36/73 |
| 7,160,275 B2 * | 1/2007 | Falconer | A61F 5/441 604/338 |
| 7,214,217 B2 * | 5/2007 | Pedersen | A61F 5/441 604/338 |
| 7,326,190 B2 * | 2/2008 | Botten | A61F 5/441 604/332 |
| 7,341,578 B2 | 3/2008 | Bulow et al. | |
| 7,604,622 B2 * | 10/2009 | Pedersen | A61F 5/441 604/338 |
| 7,655,070 B1 * | 2/2010 | Dallas | B01D 39/04 428/221 |
| 8,048,210 B2 * | 11/2011 | Dallas | B01D 39/14 428/221 |
| 8,211,218 B2 * | 7/2012 | Dallas | B01D 39/14 428/221 |
| 8,246,730 B2 * | 8/2012 | Dallas | C12N 5/0068 428/221 |
| 8,343,264 B2 * | 1/2013 | Dallas | B01D 39/1623 55/486 |
| 8,585,753 B2 * | 11/2013 | Scanlon | B29C 55/26 623/1.42 |
| 8,753,438 B2 * | 6/2014 | Dallas | B01D 39/1623 428/221 |
| 8,979,811 B2 * | 3/2015 | Keleny | B01D 46/02 604/338 |
| 9,028,858 B2 | 5/2015 | Nielsen et al. | |
| 9,168,180 B2 * | 10/2015 | Ha | A61F 13/00063 |
| 9,539,137 B2 | 1/2017 | Smith | |
| 9,610,523 B2 * | 4/2017 | Dallas | B01D 39/04 |
| 9,833,352 B2 | 12/2017 | Maidl et al. | |
| 10,058,807 B2 * | 8/2018 | Dallas | C12M 25/14 |
| 10,646,370 B2 * | 5/2020 | Keleny | A61F 5/441 |
| 11,534,324 B2 * | 12/2022 | Keleny | A61F 5/441 |
| 2003/0100870 A1 | 5/2003 | Villefrance | |
| 2003/0170453 A1 * | 9/2003 | Foss | A41B 17/00 428/375 |
| 2003/0187412 A1 * | 10/2003 | Martin | A61F 13/8405 604/359 |
| 2004/0089640 A1 | 5/2004 | Bager et al. | |
| 2004/0209059 A1 * | 10/2004 | Foss | D01F 8/14 428/292.1 |
| 2004/0214495 A1 * | 10/2004 | Foss | B32B 27/306 442/364 |
| 2005/0003728 A1 * | 1/2005 | Foss | D01F 8/12 442/394 |
| 2005/0143696 A1 * | 6/2005 | Pedersen | A61F 5/448 604/332 |
| 2007/0049880 A1 * | 3/2007 | Suehr | A61F 5/441 604/333 |
| 2007/0203466 A1 * | 8/2007 | Pedersen | A61F 5/441 604/339 |
| 2007/0207186 A1 * | 9/2007 | Scanlon | A61F 2/91 623/1.42 |
| 2009/0247970 A1 * | 10/2009 | Keleny | B01D 46/0036 156/247 |
| 2010/0010460 A1 * | 1/2010 | Butler | A61F 5/441 604/333 |
| 2010/0145291 A1 | 6/2010 | Kambara | |
| 2010/0247925 A1 | 9/2010 | Nielsen et al. | |
| 2010/0318052 A1 * | 12/2010 | Ha | A61F 13/0226 604/385.01 |
| 2011/0112492 A1 * | 5/2011 | Bharti | A61M 1/78 604/319 |
| 2011/0212090 A1 * | 9/2011 | Pedersen | A61K 39/0011 424/234.1 |
| 2011/0238024 A1 | 9/2011 | Smith et al. | |
| 2013/0317405 A1 * | 11/2013 | Ha | A61F 13/00 602/42 |
| 2015/0250931 A1 * | 9/2015 | Bharti | A61M 1/82 604/319 |
| 2016/0038345 A1 * | 2/2016 | Ha | A61F 13/0226 602/54 |
| 2016/0235581 A1 * | 8/2016 | Keleny | A61F 5/441 |
| 2017/0143533 A1 | 5/2017 | Schertiger et al. | |
| 2018/0250155 A9 * | 9/2018 | Keleny | A61F 5/441 |

(56) References Cited

U.S. PATENT DOCUMENTS

| | | | |
|---|---|---|---|
| 2019/0328581 A1 | 10/2019 | Doshi et al. | |
| 2020/0405522 A1* | 12/2020 | Keleny | A61F 5/441 |
| 2023/0225896 A1* | 7/2023 | Keleny | A61F 5/441 |
| | | | 604/333 |

FOREIGN PATENT DOCUMENTS

| | | |
|---|---|---|
| EP | 0358316 A2 | 3/1990 |
| EP | 0235928 | 4/1991 |
| EP | 0607028 | 7/1994 |
| EP | 0680295 | 8/1999 |
| EP | 1198338 | 12/2003 |
| EP | 0981311 B1 | 8/2004 |
| EP | 1875884 | 3/2011 |
| EP | 2274068 | 1/2016 |
| EP | 3096718 | 8/2020 |
| GB | 2276324 | 9/1994 |
| GB | 2287193 | 9/1995 |
| GB | 2291364 | 1/1996 |
| GB | 2302028 | 8/1997 |
| GB | 2510563 | 8/2014 |
| GB | 2549060 | 10/2017 |
| GB | 2528305 | 1/2019 |
| JP | 4571265 | 8/2010 |
| NO | 994883 | 12/1999 |
| WO | 0105573 | 1/2001 |
| WO | 20030100870 A1 | 5/2003 |
| WO | 2007030703 | 3/2007 |
| WO | 2007095363 | 8/2007 |
| WO | 2009/146076 A2 | 12/2009 |
| WO | 2009146076 | 12/2009 |
| WO | 2019120431 | 6/2019 |
| WO | 2019120438 | 6/2019 |
| WO | 2019120439 | 6/2019 |
| WO | 2021202314 | 10/2021 |

OTHER PUBLICATIONS

"Communication Pursuant to Article 94(3) EPC," for European Patent Application No. 09755439.8, dated Feb. 5, 2014 (5 pages).
"Communication Pursuant to Article 94(3) EPC," for European Patent Application No. 09755439.8, dated Jul. 22, 2013 (5 pages).
"Communication Pursuant to Article 94(3) EPC," for European Patent Application No. 16150548.2 dated Mar. 2, 2017 (4 pages).
"Communication Under Rule 71(3) EPC," for European Patent Application No. 09755439.8, dated Jul. 13, 2015 (48 pages) with text intended to grant.
"Decision on Reexamination," for Chinese Patent Application No. 200980112883.2, dated Sep. 30, 2015 (10 pages).
"Decision on Rejection," for CN Application No. 200980112883.2, dated Apr. 11, 2014 (19 pages).
"Decision Rejecting the Opposition," from European Patent Application No. 09755439.8 dated Apr. 10, 2018 (14 pages).
"Extended European Search Report," for European Application No. 09755439.8, dated Oct. 2, 2012 (7 pages).
"Final Office Action," for U.S. Appl. No. 12/414,951, dated Apr. 11, 2014 (22 pages).
"Final Office Action," for U.S. Appl. No. 14/624,202 dated Aug. 27, 2018 (15 pages).
"Final Office Action," from U.S. Appl. No. 12/414,951, dated Mar. 27, 2013, 18 pages.
"First Office Action," First Office Action from CN Application No. 200980112883.2 dated Jan. 28, 2013, 24 pages, including English translation.
"International Preliminary Report on Patentability," for PCT Application No. PCT/US2021/024509 dated Oct. 13, 2022 (8 pages).
"International Preliminary Report on Patentability," for PCT Application No. PCTUS09/039148 dated Oct. 14, 2010 (6 pages).
"International Search Report and Written Opinion," for PCT Application No. PCT/US2021/024509 dated Jul. 8, 2021 (11 pages).
"Non-Final Office Action Received," dated Jan. 19, 2012 in co-pending U.S. Appl. No. 12/414,951, "Enclosure Ventilation Filter and Assembly Method," (16 Pages)., 16.
"Non-Final Office Action," for U.S. Appl. No. 14/624,202 dated Feb. 2, 2018 (23 pages).
"Non-Final Office Action," for U.S. Appl. No. 14/624,202 dated Jun. 13, 2019 (8 pages).
"Non-Final Office Action," for U.S. Appl. No. 16/870,578 dated Apr. 13, 2022 (19 pages).
"Non-Final Office Action," from U.S. Appl. No. 12/414,951, dated Aug. 15, 2013, 16 pages.
"Notice of Allowance," for U.S. Appl. No. 12/414,951, dated Jul. 18, 2014 (11 pages).
"Notice of Allowance," for U.S. Appl. No. 14/624,202 dated Jan. 9, 2020 (11 pages).
"Notice of Allowance," for U.S. Appl. No. 16/870,578 dated Aug. 22, 2022 (12 pages).
"Notice of Allowance," For U.S. Appl. No. 12/414,951, dated Nov. 5, 2014 (10 pages).
"Opponent Submission in Response to Summons to Attend Oral Proceedings," for European Patent Application No. 09755439.8 filed Jan. 12, 2018 (9 pages).
"PCT International Search Report and Written Opinion from International Application No. PCT/US2009/039148, corresponding to U.S. Appl. No. 12/414,951, dated Nov. 24, 2009, pp. 1-11".
"Reply of The Patent Proprietor to the Notice of Opposition," European Patent Application No. 09755439.8 filed Mar. 31, 2017 (13 pages).
"Response to Communication Pursuant to Article 94(3) EPC," for European Patent Application No. 09755439.8, dated Feb. 3, 2014 and filed with the EPO Jun. 12, 2014 (8 pages).
"Response to Extended European Search Report," Response to Extended European Search Report, dated Oct. 19, 2012, Filed in the European Patent Office on Apr. 25, 2013 for EP Patent Application No. 09755439.8.
"Response to Final Office Action," for U.S. Appl. No. 16/870,578, filed Jul. 8, 2022 (7 pages).
"Response to Non Final Office Action," for U.S. Appl. No. 14/624,202, filed May 2, 2018 (9 pages).
"Restriction Requirement Received," dated Sep. 21, 2011 in co-pending U.S. Appl. No. 12/414,951, "Enclosure Ventilation Filter and Assembly Method" (6 pages), 6.
"Second Office Action," for Chinese Application No. 200980112883.2, dated Sep. 23, 2013 (16 pages) with English Translation.
"Summons to Attend Oral Proceedings Pursuant to Rule 115(1) EPC," for European Patent Application No. 09755439.8, mailed Jul. 14, 2017 (9 pages).
"Third Office Action," for Chinese Patent Application No. 200980112883.2, dated Dec. 18, 2015 (8 pages) with translation.

* cited by examiner

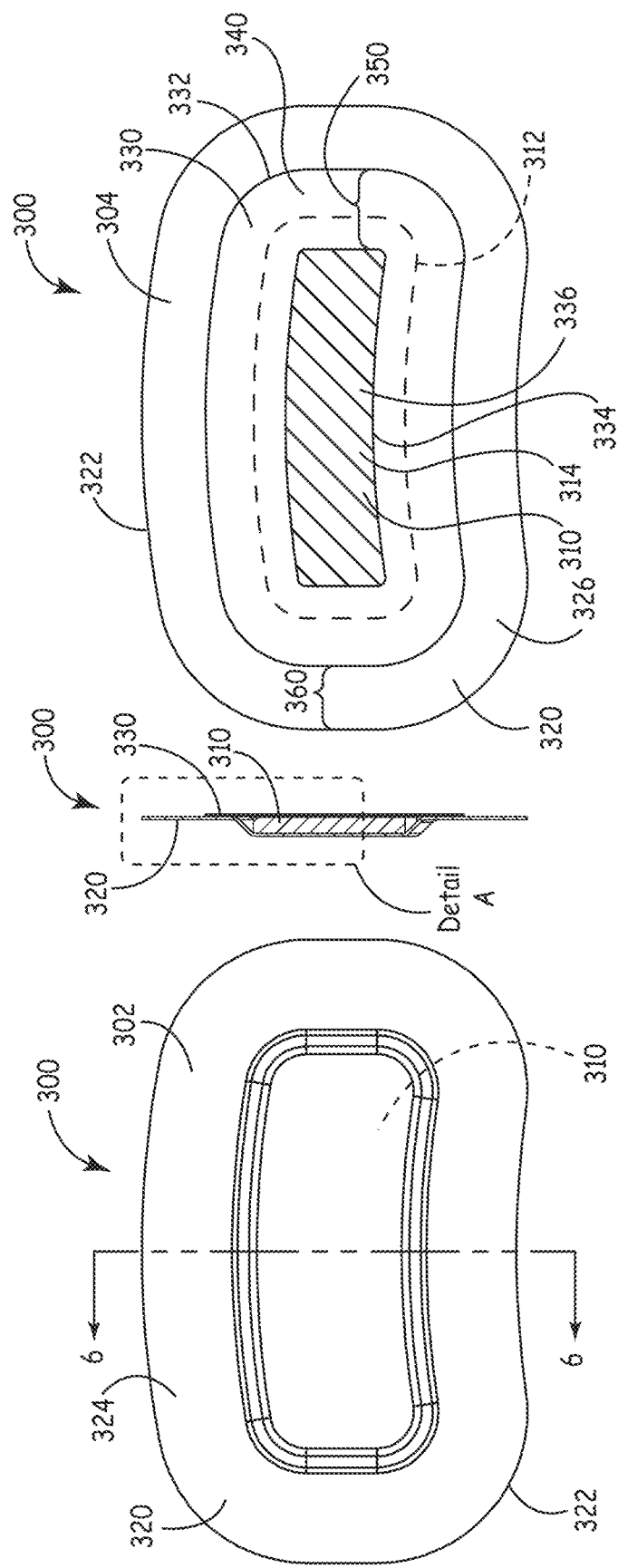

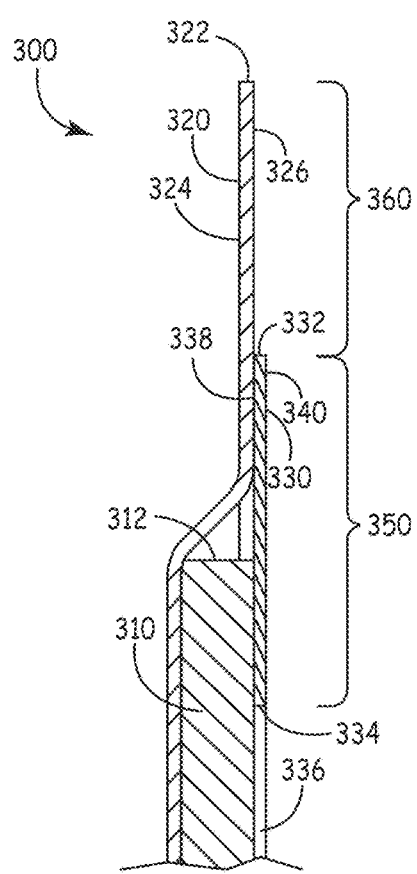 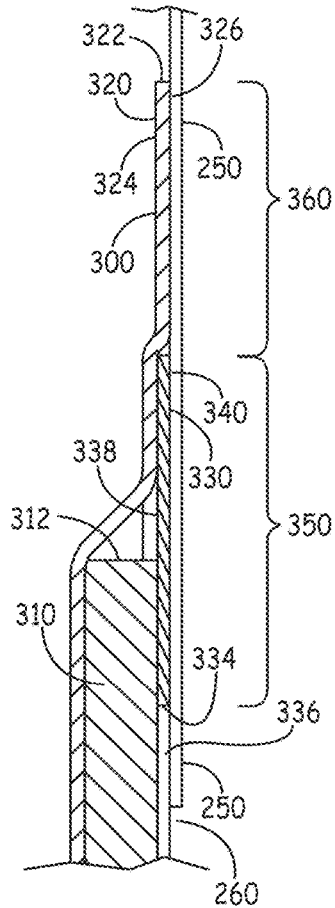 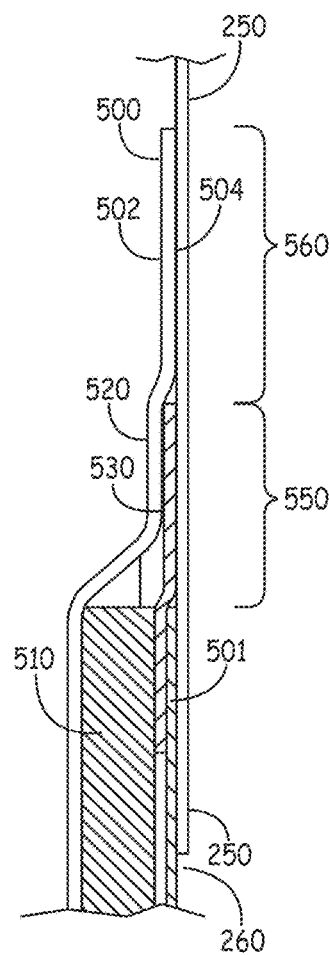
FIG. 7  FIG. 8  FIG. 9
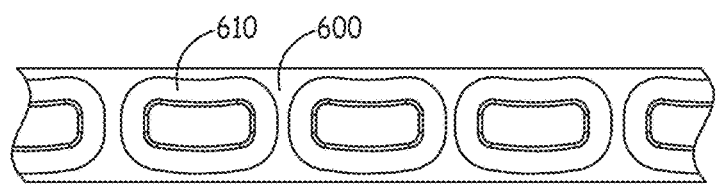
FIG. 10

ENCLOSURE VENTILATION FILTER AND ASSEMBLY METHOD

PRIORITY

This application is a continuation of U.S. patent application Ser. No. 16/870,578, filed on May 8, 2020, which is a division of U.S. patent application Ser. No. 14/624,202, filed on Feb. 17, 2015, which is a continuation of U.S. patent application Ser. No. 12/414,951, filed on Mar. 31, 2009, which claims the benefit of U.S. Provisional Patent Application Ser. No. 61/041,244, entitled "Ostomy Bag Ventilation Filter," filed Apr. 1, 2008, the contents of which are herein incorporated by reference in its entirety.

FIELD OF THE INVENTION

The present invention relates to absorbent breather filters for enclosures, such as bags, and more particularly ostomy bags, and more particularly, to ventilation filters and assemblies for ostomy bags.

BACKGROUND OF THE INVENTION

An ostomy (also referred to as a colostomy, ileostomy or urostomy) is a type of surgery required when a person loses normal bladder or bowel function due to birth defect, disease, injury or other disorder. Cancer patients account for about 80 percent of ostomies. Following an ostomy, bodily waste needs to be expelled through a stoma (surgical opening) on the abdominal wall and into a special appliance called an ostomy bag.

Depending on a patient's diet, age, diagnosis, activity level, and other variables, these wastes can contain significant amounts of gases, such as amines, ammonia, and mercaptains. These gases can inflate the ostomy bag, creating concern or discomfort for the patient, and compromise the seal between the skin and the bag itself.

In the past, ostomy bags have been provided with deodorizing gas filters so that flatus gases can be vented from the bag to reduce or prevent ballooning and, at the same time, to deodorize the escaping gases. In an effort to prevent such a filter from becoming clogged and rendered ineffective by liquid and/or solid body waste material within the bag, it has been common either to secure the filter to the outside surface of the bag over a vent opening, or to provide protection for an internally-mounted filter in the form of a porous membrane that extends over the filter. Typically this internally-mounted filter is hydrophobic and may also be oleophobic.

Ostomy bag filters may be of the axial flow type, as shown in FIG. 1, or more commonly the so-called radial flow type or lateral flow type, as shown in FIG. 2. In the axial flow filter 100, the air to be filtered flows in a straight path from a first side 104 to a second side 106, directly or axially though the filter media 108. In contrast, the term lateral flow or radial flow means that the gases flow along the plane of a relatively flat filter, as shown in filter 200 of FIG. 2. In FIG. 2, the gases flow from a first side 204 to a second side 206 by entering the filter media 208 at its outer edge 210 and flowing toward a center 212 of the filter media. Filter layers can also be configured so that the gas flows from one end of a filter media to another end, or in many different types of flow paths. For ostomy bag applications, a filter of the radial or lateral flow type is most common because it allows for the construction of a low-profile filter that also provides an extended flow path for deodorizing the flatus gases.

SUMMARY OF THE INVENTION

In one embodiment, a filter assembly for an enclosure is described having herein, having an enclosure side, a first layer which is gas permeable, and an adsorbent layer comprising adsorbent particles dispersed in a fine fiber web. The enclosure side of the filter assembly includes an adhesive zone in which adhesive is present having an outer adhesive perimeter and a weld area surrounding at least a portion of the adhesive zone, where the filter assembly is heat-sealable to the enclosure at the weld area.

In another embodiment, an ostomy filter for an ostomy bag is described, where the ostomy bag is configured to contain bodily waste products, comprising a bag side and an outer side opposite from the bag side, a first layer which is gas permeable and liquid impermeable, and an adsorbent layer of adsorbent particles dispersed in a fine fiber web. The bag side of the ostomy filter includes an adhesive zone in which adhesive is present, the adhesive zone having an outer adhesive perimeter and an inner adhesive perimeter, wherein the inner adhesive perimeter surrounds an exit opening. The bag side also includes a weld area surrounding the adhesive zone, where the filter assembly is heat-sealable to the enclosure bag at the weld area.

In another embodiment, a method for attaching a filter assembly to an enclosure over a vent opening in the enclosure includes providing an enclosure bag, where the enclosure bag includes a vent opening, providing a filter assembly on a release liner, the filter assembly having a bag side and an outer side opposite from the bag side. The bag side of the filter includes an adhesive zone in which adhesive is present having an outer adhesive perimeter and a weld area surrounding at least a portion of the adhesive zone, where the filter assembly is heat-sealable to the enclosure bag at the weld area. The method further includes removing the filter assembly from the release liner to reveal the adhesive zone, placing the filter assembly on the enclosure bag over the vent opening, and after placing the filter on the enclosure bag, forming a seal between the filter assembly and the enclosure bag.

The invention may be more completely understood by considering the detailed description of various embodiments of the invention that follows in connection with the accompanying drawings.

BRIEF DESCRIPTION OF THE DRAWINGS

FIG. 4 is a bottom view of a filter assembly in accordance with one embodiment.

FIG. 5 is a top view of the filter assembly of FIG. 4.

FIG. 6 is a cross-sectional view of the filter assembly of FIG. 4, taken along line 6-6 of FIG. 5.

FIG. 7 is a cross-sectional view of the filter assembly of FIG. 4, for Detail Section A shown in FIG. 6.

FIG. 8 is a cross-sectional view of the filter assembly of FIG. 4, adhered to an ostomy bag.

FIG. 9 is a cross-sectional view of another embodiment of a filter assembly, having a second cover layer, adhered to an ostomy bag.

FIG. 10 is a top view of a release liner carrying multiple filter assemblies.

Figure 1:
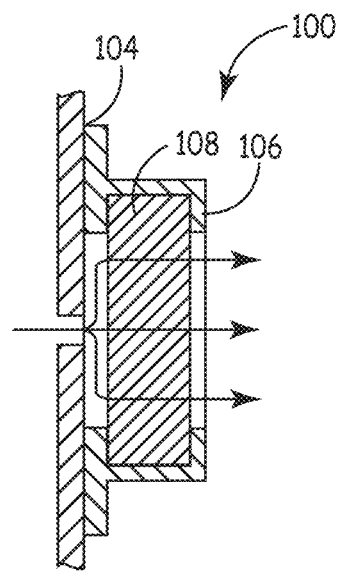
FIG. 1 is a depiction showing axial flow through a prior art air filter.
Figure 2:
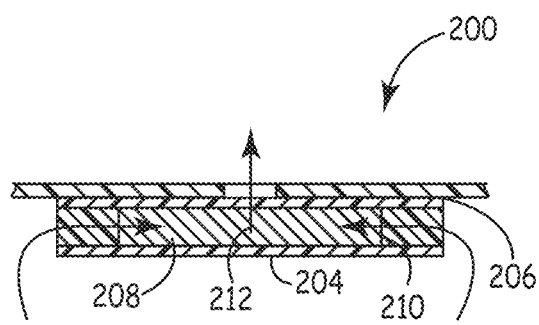
FIG. 2 is a depiction showing lateral flow through a prior art air filter.

While the invention may be modified in many ways, specifics have been shown by way of example in the drawings and will be described in detail. It should be understood, however, that the intention is not to limit the invention to the particular embodiments described. On the contrary, the intention is to cover all modifications, equivalents, and alternatives following within the scope and spirit of the invention as defined by the claims.

DETAILED DESCRIPTION OF THE INVENTION

A filter assembly is described herein including, in certain embodiments, a filter layer or adsorbent layer of adsorbent particles substantially uniformly dispersed in a fine fiber web, plus at least one outer gas permeable film layer, which will be referred to as a first layer. The first layer is heat sealable in some embodiments and is microporous in some embodiments. The filter assembly has a low profile and is capable of selective gas adsorption, absorption, catalysis, or combination of each. This type of filter assembly can be placed over a vent as a vent assembly and is often referred to as an Adsorbent Breather Filter (ABF).

ABF's are most commonly used to seal a breather hole in liquid tight enclosures. Vented ostomy bags, where liquid and solid phase materials are trapped while select gases are allowed to escape, is an example where the filter assembly described herein is particularly useful. ABF's are also commonly used in sensor and electronic enclosures where the focus is on keeping solids and liquids outside the enclosure while allowing select gas phase fluid to enter for cooling and/or sensing purposes.

The filter assembly can be used with many different types of enclosures, both flexible and rigid. In one embodiment, the enclosure is a bag, which is a flexible enclosure made mostly of plastic. The filter assembly is particularly useful in the context of its use with an ostomy bag, so it will be described herein in that context for convenience. The filter assembly has two sides: a bag side or enclosure side to be sealed to an ostomy bag or other enclosure, and an outer side opposite from the bag side. For convenience, the enclosure side of the filter assembly will be referred to as the bag side herein, and the filter assembly will generally be discussed in the context of an enclosure bag, specifically, an ostomy bag, although the concepts herein are equally applicable to other types of enclosures.

On the bag side of the filter, adhesive is present in an adhesive zone which has an outer perimeter. Surrounding the outer perimeter of the adhesive zone, the filter is heat-sealable to the ostomy bag. The bag side of the filter has a weld zone where the filter can be heat-sealed to the ostomy bag. In some embodiments, the weld area completely surrounds the adhesive zone. In some embodiments, the weld area is adjacent to the adhesive area along the entire outer perimeter of the adhesive zone. In some embodiments, the weld zone partially overlaps the adhesive zone along the outer adhesive perimeter. In some embodiments, the adhesive is a pressure sensitive adhesive.

The combination of the adhesive and the weld zone facilitates accurate and efficient assembly, and reliable seal formation between the bag and filter. In one embodiment of an assembly process, an ostomy bag filter assembly is provided on a release liner. The filter assembly is placed over a vent opening in an ostomy bag that is configured to contain bodily waste products. First, the filter is removed from the release liner to reveal the adhesive zone on the bag side of the filter. The filter is then placed on the ostomy bag over the vent opening, so that the bag side of the filter and the adhesive zone contacts the bag surrounding the vent opening. Preferably, some pressure is used when placing the filter on the bag, so that the adhesive is activated to secure the filter to the bag, forming a preliminary seal. After placing the filter on the ostomy bag, a permanent seal is formed between the filter and the bag. The permanent seal may be formed by heat sealing. The adhesive holds the filter in the correct position during the assembly process.

The heat sealing may be accomplished by many different techniques, including the application of heat, the application of radio-frequency waves, the application of ultrasonic waves, or other techniques.

In one embodiment, the bag side of the ostomy filter is adhered to an interior surface of the ostomy bag over a vent opening in the bag. In another embodiment, the bag side of the ostomy filter is adhered to an exterior surface of the ostomy bag over a vent opening in the bag.

Embodiments of the adsorbent layer described herein typically incorporate an activated carbon and fiber matrix consisting of finely divided activated carbon particles constrained by fine fibers, such as electrospun polymeric fine fibers. The activated carbon and fiber matrix is then laminated and/or encapsulated by various micro-porous and/or non-porous films to create a highly effective and low profile ostomy vent capable of selective gas adsorption, catalysis, or combination of each.

The first layer of the filter assembly is gas permeable. The first layer is also microporous. The term "microporous" as used herein refers to a material containing pores with diameters of about 2 microns or less than 2 microns. In one embodiment, the first layer is also liquid impermeable. In one embodiment, the first layer includes expanded polytetrafluoroethylene (ePTFE). In one embodiment, the first layer is a laminate including an ePTFE layer and a scrim layer. The first layer has a thickness of at least 0.5 mils (0.013 mm) in one embodiment, and at most 35 mils (0.9 mm) in one embodiment.

The ostomy filter can further include a second layer that is gas permeable, in some embodiments. The first layer can be positioned on an outer face of the adsorbent layer and the second layer can be positioned on a bag face of the adsorbent layer. The first and second layers are coextensive over the filter assembly in one embodiment. In another embodiment, the second layer is coextensive with at least the adsorbent layer. The filter assembly may be sealed to the ostomy bag at a continuous outer periphery region that contains the adsorbent layer around its full periphery circumference.

The reactive or adsorptive particles are held together or interspersed with fibers. The combination of particles and fibers results in a material that offers several advantages: increased diffusion; allowing for the use of smaller particles, thereby increasing the external surface area and hence the reaction rate; and increased permeation into the reactive layer.

The low pressure drop and high efficiency of the particle and fiber construction allows the filter to be constructed with airflow through the face of the filter media in an axial configuration. The flexibility and thin profile of the activated carbon and fiber matrix based filter allow the ostomy product to conform more closely to the patient's body. The filter described herein comprises, in certain embodiments, at least one outer sealable liquid impermeable, gas permeable microporous film layer; plus an inner filter layer of adsorbent particles substantially uniformly dispersed in a fine fiber web. In some embodiments, the filter further also includes a second outer porous cover layer.

The reactive or adsorptive particles can be held together or interspersed with fibers. The combination of particles and fibers results in a material that offers several advantages: increased diffusion; allowing for the use of smaller particles, thereby increasing the external surface area and hence the reaction rate; and increased permeation into the reactive layer.

In one implementation, the carbon particle loading level is between 100 and 500 $g/m^2$, in certain implementations the carbon particle loading level is between 150 and 400 $g/m^2$, while in other implementations the carbon particle loading level is between 200 and 300 $g/m^2$. Typically the carbon particle loading is at least 50 $g/m^2$, commonly more than 100 $g/m^2$, and optionally more than 200 $g/m^2$.

The adsorbent layer having adsorbent particles substantially uniformly dispersed in the fine fiber will often have a thickness of less than 5 mm, optionally less than 3 mm, and desirably less than 2 mm. In one embodiment, the adsorbent layer has a thickness of at least 0.01 mm. In one embodiment, the adsorbent layer has a thickness of not more than 10 mm. The adsorbent layer can have a thickness that is at least 10 mil (0.25 mm). In one embodiment, the adsorbent layer has a thickness that is at most about 250 mil (6.35 mm). In one embodiment, the adsorbent layer is about 50 mil (1.27 mm) thick.

First Embodiment

Figure 3:
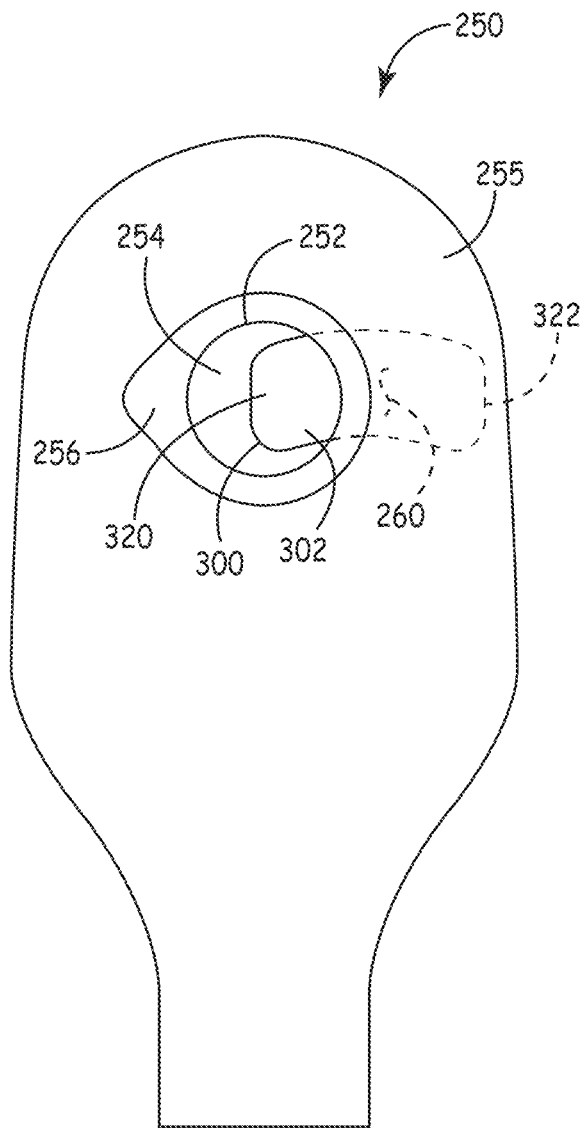
FIG. 3 is a top view of an ostomy bag having a filter assembly in accordance with one embodiment.

A first embodiment of a filter assembly for use with an ostomy bag is shown in FIGS. 3-8. FIG. 3 is a top view of an ostomy bag 250 having a filter assembly 300 in accordance with one embodiment. The ostomy bag 250 includes a stoma opening 252 into an interior 254 of the bag. The opening 252 is surrounded by a flange 256, which is where the ostomy bag will be connected to the user's stoma. The bag 250 also defines a vent opening 260. The filter 300 is secured to an interior side of the ostomy bag 250, so that the filter covers the vent opening 260. The outline of the filter 300 is visible through the stoma opening 252, and is shown in dashed lines where it is hidden by a top layer of the ostomy bag.

The filter 300 has a bag side that is secured to the bag, and an outer side, which is opposite to the bag side. The outer side 302 is visible in FIG. 3 through the stoma opening, as well as in FIG. 5, while FIG. 4 is a plan view of the bag side 304 of the filter 300. FIG. 6 is a cross-sectional view of the filter 300 along line 6-6 in FIG. 5. Referring to FIGS. 4-6, the filter includes an adsorbent layer 310, a first layer 320 and an adhesive layer 330. The first layer 320 has an outer perimeter 322, an outer side 324 and a bag side 326. The adhesive layer 330 has an outer adhesive perimeter 332 and an inner adhesive perimeter 334, as well as an outer side 338 and a bag side 340. The inner perimeter 334 defines an exit window 336, through which gases will exit from the ostomy bag. An outer perimeter 312 of the adsorbent layer is shown in dashed lines through the adhesive layer. The bag side 314 of the filter layer or adsorbent layer 310 is visible in FIG. 4 through the exit window 336.

The bag side 304 of the filter 300 includes two areas that are important for the attachment process: an adhesive zone 350 and a weld area 360. The adhesive zone 350 is defined on the bag side 340 of the adhesive layer 330. The adhesive zone includes pressure sensitive adhesive in one embodiment. In one embodiment, the adhesive layer 330 is a pressure sensitive tape. One example of a pressure sensitive double-sided tape that is suitable for the filter assembly described herein is 3M 9495 LE, Double Sided Tape available from 3M of St. Paul, Minnesota.

The weld area 360 surrounds at least a portion of the adhesive zone. In one embodiment, the weld area completely surrounds the adhesive zone. In one embodiment, the weld area is adjacent to the adhesive zone along the outer adhesive perimeter 332. In one embodiment, the weld area is continuously adjacent to, but not overlapping, the adhesive zone. In the embodiment of FIGS. 4-7, the weld area both completely surrounds the adhesive zone, and partially overlaps the adhesive zone along the outer adhesive perimeter 332.

FIG. 7 is a cross-sectional view of the filter 300, enlarged to show Detail A in FIG. 6, and showing the adsorbent layer 310, the first layer 320 and the adhesive layer 330. In one embodiment, the adhesive layer 330 includes a pressure-sensitive adhesive on both the outer side 338 and the bag side 340. The adhesive on the bag side of the adhesive layer is used to secure the adsorbent layer to the assembly and to secure the first layer to the assembly.

The width of the adhesive zone is at least 1.5 mm in one embodiment, and at least 2 mm in another embodiment. In one example, the adhesive zone is 6 mm wide, and in another, 8 mm wide. In one embodiment, the width of the adhesive zone is at most 15 mm wide, and in another, 20 mm wide.

The dimensions of the first layer, and therefore of the outer perimeter of the overall filter assembly, can vary based on the size of the enclosure that is being vented, based on the size of the vent opening and many other factors. In various embodiments, the first layer has a width of at least 5 mm, at least 10 mm, and at least 15 mm. In one embodiment, the first layer has a width of 23 mm, and in another 20 mm. In one embodiment, the width of the first layer is at most 30 mm, and in another, at most 40 mm. In various embodiments, the first layer has a length of at least 10 mm, at least 20 mm, and at least 20 mm. In one embodiment, the first layer has a width of 35 mm, and in another 38 mm. In one embodiment, the width of the first layer is at most 45 mm, and in another, at most 50 mm. The first layer has a thickness of at least 0.5 mils (0.013 mm) in one embodiment, and at most 35 mils (0.9 mm) in one embodiment.

FIG. 8 is a cross-sectional view similar to FIG. 7, but showing the filter 300 welded to a bag 250. The vent opening 260 is present in the bag 250, and is positioned to align with the exit window 336 of the adhesive layer 330.

An inner adhesive perimeter 334 surrounds and defines an exit window 336, from which gases exit the filter assembly. The adhesive zone 350 overlaps an outer perimeter 312 of the adsorbent layer 310. As a result, the adhesive zone 350 prevents the bypass of the adsorbent layer 310 during use. In one embodiment, adhesive is also present on an outer side 338 of the adhesive layer 330. This adhesive area secures the adsorbent layer to the first layer, and can prevent bypass of the adsorbent layer.

Second Embodiment

FIG. 9 is a cross-sectional view similar to FIG. 8, but showing a second embodiment of a filter assembly 500 having a second gas permeable layer 501, which is also liquid impermeable. The filter assembly 500 has a bag side 504 and an outer side 502. The filter assembly also includes an adsorbent layer 510, a first layer 520 and an adhesive layer 530. The adsorbent layer 510 is sandwiched between the first layer 520 and the second layer 501. The adhesive layer 530 is present between the second layer 501 and the adsorbent layer 510, so that an adhesive zone 550 is present on the bag side 504 of the filter assembly 500.

Other aspects of the filter assembly 500 are similar to the filter assembly 300. For example, the filter assembly 500 also defines a weld zone 560 where the filter assembly 500 is welded to the bag.

The second layer of the filter assembly is also microporous and liquid impermeable. In one embodiment, the second layer includes expanded polytetrafluoroethylene (PTFE). In one embodiment, the second layer is a laminate including a PTFE layer and a scrim layer. The second layer has a thickness of at least 0.1 mil (0.0025 mm) in one embodiment, and at most 15 mil (0.38 mm) in one embodiment. The second layer has a thickness of at least 0.5 mils (0.013 mm) in one embodiment, and at most 5 mil (0.13 mm) in one embodiment.

The inclusion of the second layer can serve to prevent liquid from entering the ostomy bag or other enclosure. This can be especially useful if the user wears the bag while showering, bathing or engaged in similar activities. In another embodiment, a filter assembly without a second layer can be provided with a different method of protection against liquid entering the bag. The user can be provided with a sealing sticker that is liquid impermeable to place over the vent opening while engaged in such activities.

Lateral Flow Embodiment

Figure 17:
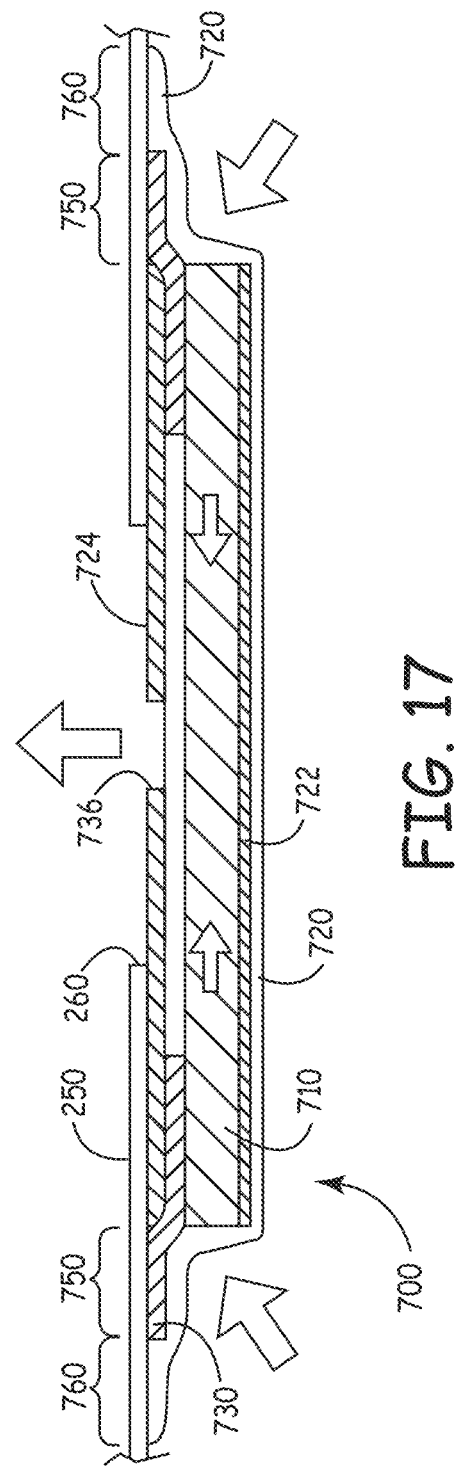
FIG. 17 is a cross-sectional view of another embodiment of a filter assembly described herein having a lateral flow path.

FIG. 17 is a cross-sectional view of a filter assembly 700 positioned on an enclosure wall of ostomy bag 250, where the filter assembly has a lateral flow path through a filter layer or adsorbent layer 710. The filter assembly 700 includes a first layer 720 and an adhesive layer 730. An adhesive zone 750 is defined by the adhesive layer 730. A weld zone 760 is defined outside of the adhesive zone 750 and surrounding the adhesive zone 740, where the first layer can be sealed to the enclosure wall 250. The enclosure wall of ostomy bag 250 defines a vent opening 260.

Two gas impermeable barriers 722, 724 are used to establish a lateral flow path. The first barrier layer 722 is positioned on an outer side of the adsorbent layer 710, so that gas cannot enter along that side of the adsorbent layer 710. Instead, gas must enter along a perimeter edge of the adsorbent layer 710, and flow laterally toward the center of the adsorbent layer. The second barrier layer 724 defines an exit opening 736 near the center of the filter assembly, through which gas can flow to exit the filter assembly.

Mixed Flow Embodiment

Figure 18:
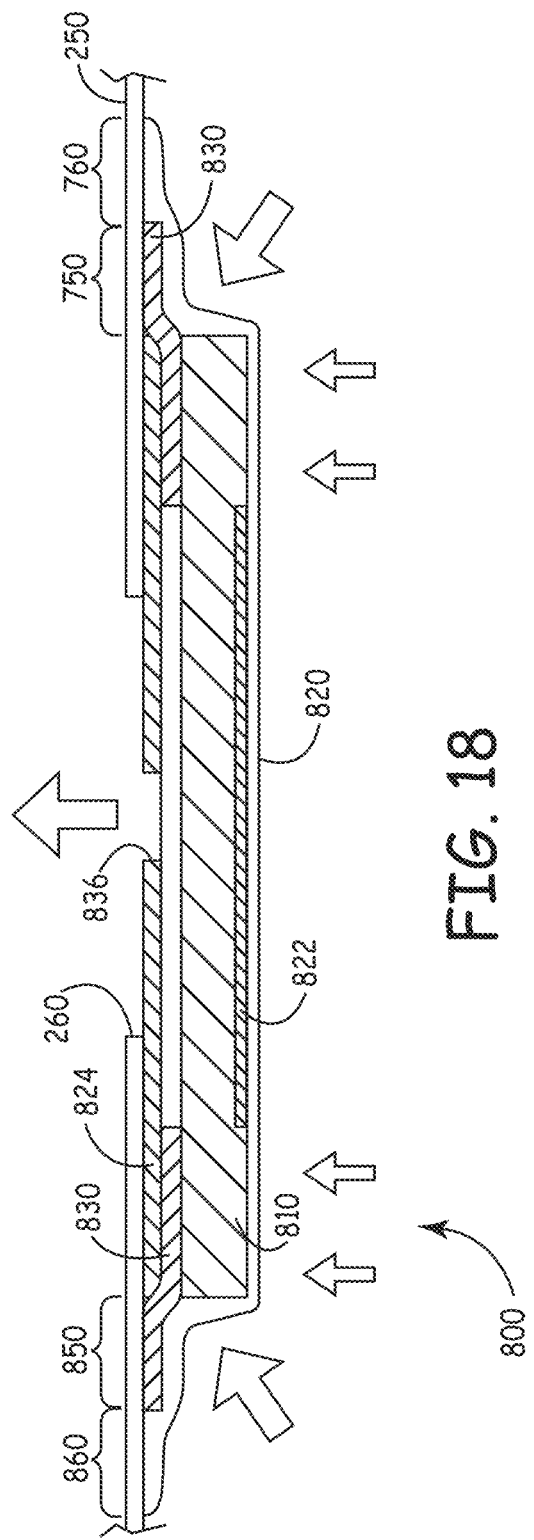
FIG. 18 is a cross-sectional view of yet another embodiment of a filter assembly described herein having flow paths with lateral and axial aspects.

FIG. 18 is a cross-sectional view of a filter assembly 800 positioned on an enclosure wall 250 having an exit opening 260, where the filter assembly permits air flow in both axial and lateral paths through a filter layer or adsorbent layer 810. The filter assembly 800 includes a first layer 820 and an adhesive layer 830. An adhesive zone 850 is defined by the adhesive layer. A weld zone 860 is defined outside of the adhesive zone 850 and surrounding the adhesive zone 850, where the first layer can be sealed to the enclosure wall 250.

Two gas impermeable barriers 822, 824 are used to guide the gases toward a lateral flow path, but also permit a more axial flow path. The first barrier layer 822 is positioned on a central portion of an outer side of the adsorbent layer 810, so that gas can enter only along a perimeter edge of the adsorbent layer 810, or along an outer portion of the outer side of the adsorbent layer. The gases then flow laterally or axially and laterally toward the center of the adsorbent layer. The second barrier layer 824 defines an exit opening 836 through which gas can flow.

The FIGS. are not drawn to scale, in order to illustrate the various layers more clearly. For example, the barrier layers of FIGS. 17 and 18 are relatively thin compared to the rest of the layers in the assembly. An example of a barrier film for use as a first barrier layer and a second barrier layer in the embodiments of FIGS. 17 and 18 is a film of polyethylene terephthalate (PET) having a thickness of at least 0.5 mil (0.013 mm). In various embodiments, the PET film has a thickness of not more than 2 mil (0.05 mm), 3 mil (0.76 mm), and 5 mil (0.13 mm).

Assembly Method

FIG. 10 is a top view of a release liner 600 with multiple filter assemblies 610 positioned on the release liner. An adhesive zone on the side of the filter assemblies that is contacting the release liners holds the filter assemblies to the release liner.

In one example of an assembly method, an ostomy bag 250 (FIG. 3) is provided, where the ostomy bag is configured to contain bodily waste products. The ostomy bag includes a stoma opening 252, an interior surface 254, an exterior surface 255 and a vent opening 260. A filter assembly, such as filter assembly 300 or 500, is provided on a release liner 600. The filter assembly has a bag side and an outer side opposite from the bag side. The bag side of the filter includes an adhesive zone in which adhesive is present, where the adhesive zone has an outer perimeter. The adhesive zone may also have an inner perimeter that surrounds an exit window for gases from the ostomy bag. The filter assembly also includes a weld area that at least partially surrounds the adhesive zone, where the filter assembly is heat sealable to the bag.

The filter assembly is removed from the release liner to reveal the adhesive zone on the bag side of the filter. The filter is then placed on the ostomy bag over the vent opening, so that the bag side of the filter and the adhesive zone contacts the bag surrounding the vent opening. Preferably, some pressure is used when placing the filter on the bag, so that the adhesive is activated to secure the filter to the bag, forming a preliminary seal. After placing the filter on the ostomy bag, a permanent seal is formed between the filter and the bag. The permanent seal may be formed by heat sealing. The adhesive holds the filter in the correct position during the assembly process, and then the heat seal creates the permanent seal to prevent gaseous or liquid by-pass of the filter assembly. The heat seal is accomplished by applying heat to the first layer, so that it creates a bond with the bag material.

In one embodiment, the bag side of the ostomy filter is adhered to an interior surface 254 of the ostomy bag over a vent opening in the bag. In another embodiment, the bag side of the ostomy filter is adhered to an exterior surface 255 of the ostomy bag over a vent opening in the bag.

The embodiments described allow for a convenient and efficient assembly method with a highly reliable seal between the bag and the filter assembly. One of the most convenient ways of connecting an ostomy filter to an ostomy bag would be to use only a pressure-sensitive adhesive to create the seal between the bag and the filter. With only pressure-sensitive adhesive and no heat seal, there is no need for the equipment that is used to create the seal. There is also no need for the equipment needed to apply other types of adhesive. The people assembling the bags would simply expose the adhesive and place the filter over the vent opening. In contrast, the use of a heat sealing process requires preparation of the heat sealing equipment, the careful placement of the filter over the vent opening, and maintaining the typically small and lightweight filter in that position while the heat sealing equipment is precisely applied. However, ostomy bags are typically made with materials having a low surface energy, such as ethylene vinyl acetate (EVA) plastic, because the low surface energy of the material makes it easy to completely empty the bag when necessary. But the low surface energy of the bag material causes concern that the pressure-sensitive adhesive seal will not be reliable. Any leakage at the filter assembly would be unacceptable.

As a result, heat sealing of the ostomy filter to the bag has been the dominant method of assembly for ostomy bags and adhesive-only seals using pressure-sensitive adhesive have not been considered sufficiently reliable. The embodiments described herein provide a convenient solution to the manufacturers of ostomy bags. The presence of an adhesive zone on the bag side of the filter assembly causes the filter assembly to stay where it is placed until the heat sealing equipment is applied to the filter assembly, allowing for a more efficient assembly process.

The adhesive provides a seal around the adsorbent layer, while the heat seal provides a further safeguard against solid or liquid leakage. Since the adhesive is providing a seal around the adsorbent layer, there are fewer constraints on the shape and size of the heat welded area, so these embodiments also allow greater design freedom for different part shapes and sizes.

Polymeric Fine Fibers

Figure 11:
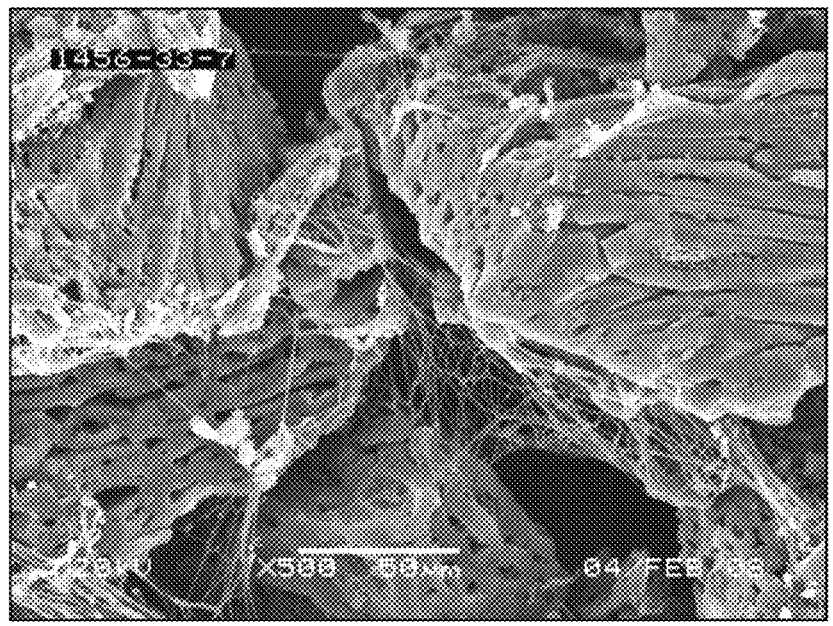
FIG. 11 is a cross-sectional view of an activated carbon and fiber matrix in accordance with one embodiment.
Figure 12:
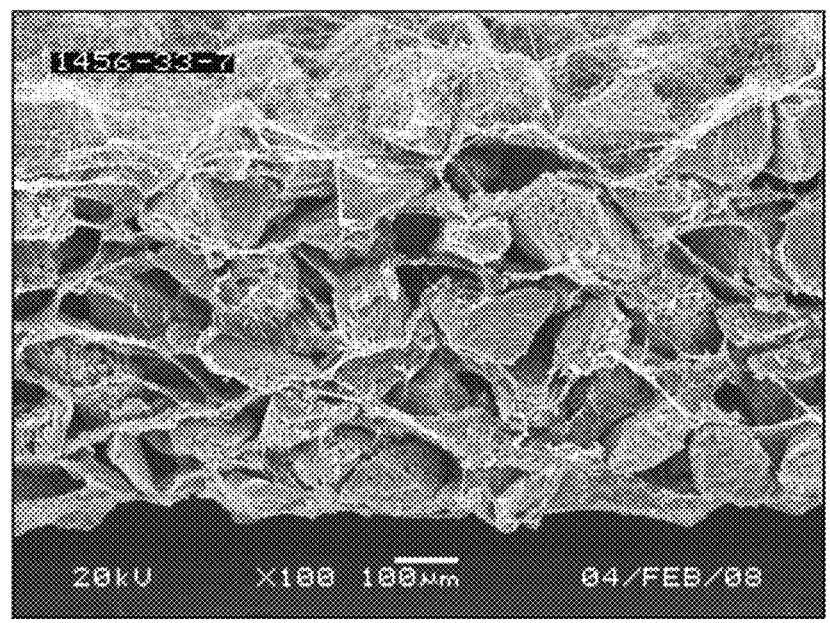
FIG. 12 is a second cross-sectional view of an activated carbon and fiber matrix in accordance with another embodiment.
Figure 13:
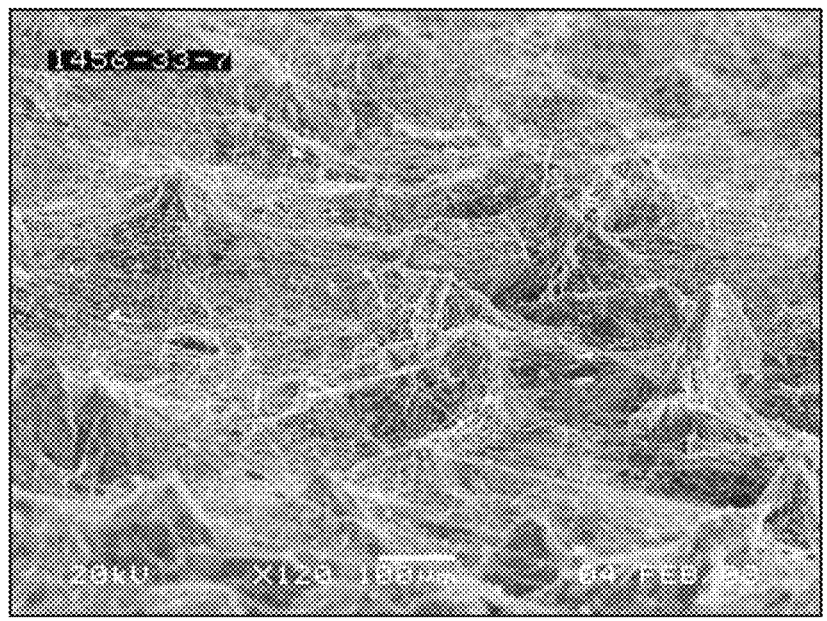
FIG. 13 is a top view of an activated carbon and fiber matrix made in accordance with another embodiment.

As described above, in certain implementations the adsorbent layer or filter media described herein utilizes a fiber matrix into which activated carbon particles or fibers are incorporated. In reference now to FIGS. 11 to 13, scanning electron micrographs (SEM's) of electrospun polymeric fine fibers are shown. These fine fibers are also referred to as nanofibers. No additional binders or other non-active materials are generally needed to construct the activated carbon and fiber matrix. As the micrographs depict, binding the particles with fine fiber minimizes void space, resulting in a near optimal adsorption capacity per given volume while providing the tortuous path necessary for the gases to diffuse. The soft, strong, and flexible nature of the fine fiber makes the activated carbon and fiber matrix an ideal structure for use as a wearable adsorbent/absorbent.

A fiber matrix that can be used is described in Published PCT Patent Application WO2007/095363, which is hereby incorporated by reference in its entirety. The fiber has a diameter of about 0.001 to about 2 microns, 0.001 to about 1 micron, 0.001 to about 0.5 micron, or 0.001 to about 5 microns, A variety of techniques can be used for the manufacture of small diameter fine fibers. One method involves passing polymeric material through a fine capillary or opening either as a melted material or in a solution that is subsequently evaporated. Fibers can also be formed by using "spinnerets" typical for the manufacture of synthetic fiber such as nylon. Electrostatic spinning is often the method of choice for forming the fine fiber nonwoven webs of the invention. Such techniques involve the use of a hypodermic needle, nozzle, capillary or movable emitter. These structures provide liquid solutions of the polymer that are then attracted to a collection zone by a high voltage electrostatic field. As the materials are pulled from the emitter and accelerate through the electrostatic zone, the fiber becomes very thin and can be formed in a fiber structure by solvent evaporation.

Another method involves using meltblown plastic or polymeric material to generate substantially uniformly dispersed fine fiber web. In general, meltblown fibers typically useable according to the present invention are an air laid continuous extrusion of fibers joined to each other to form a sheet of layer of filter material. The adsorbent particles of the present invention can be substantially uniformly dispersed in the fine fiber web. Plastics such as polypropylene, polystyrene, and polyester may be used.

Incorporation of Adsorptive and Reactive Particles

In an example method, particles are incorporated into the fine fiber nonwovens generally by feeding the particles into a flow of polymer solution using a volumetric screw feeder with an auger. In some embodiments it is advantageous to further use a deflocculator to divide agglomerated particles. The particles are then deposited along with the polymer solution and become entangled within the fine fiber network as it forms upon drying of the polymer solution. In typical embodiments the particles are activated carbon.

It will be appreciated that more than one type of particle is easily incorporated into the webs of the invention by providing a particle mix in the volumetric screw feeder; or by providing more than one feeder supplying particles to the flow of polymer solution. In this way, different particles are easily incorporated into the web.

Various embodiments allow use of a web comprising fine fiber and reactive, adsorptive or absorptive, inert or chemically modified particulates. Chemical modification is in the form of chemical or thermal treatment of the polymers, fibers and/or particulates or in the form of chemical impregnation of the particulates. It also includes mixing impregnates within the fiber/particulate web. Fluid passing through the web (typically a gas) interacts with the chemically- or thermally-modified web constituents. The active particulates can react with, absorb, or adsorb a portion of the fluid. It can allow selective chemical reactions of particular compounds or species in the fluid with other compounds or species attracted to or trapped on the surface. The surface of the particulates can also play the role of a catalyst through providing active sites that catalytically alter the material that passes through the web.

The particulates may be impregnated with a single or several impregnates, such as impregnation of activated carbon with sodium hydroxide alone for $H_2S$ removal or impregnation of a mixture of sodium hydroxide and potassium iodide. This latter composition has a higher adsorption capacity and efficiency for removal of $H_2S$ than activated carbon impregnated with sodium hydroxide. It is believed that the potassium iodide enhances the action of the sodium hydroxide catalytically or synergistically. Potassium iodide plays the role of oxidant which promotes oxidation of $H_2S$ to sulfur. In this particular case, the concepts taught herein can be applied as ostomy bag filters for $H_2S$ removal where the web with its constituents in this invention will provide the conditions required for ostomy bag filters such as low flow, low pressure drop, high $H_2S$ capacity. Other usable impregnates include citric acid, potassium hydroxide, potassium carbonate, sodium carbonate, potassium bicarbonate, sodium bicarbonate, and/or moisture, among others. Those compounds can be either impregnated on the particulates or mixed with the web constituents.

A few examples of impregnates on activated carbons and their applications include: Activated carbons impregnated with potassium carbonate for the removal of acid gases (HCl, HF, $SO_2$, $H_2S$, $NO_2$); activated carbons impregnated with potassium iodide for the removal of $H_2S$ and $PH_3$; activated carbons impregnated with iron oxide for the removal of $H_2S$ and mercaptan; and activated carbons impregnated with potassium permanganate for the removal of $H_2S$ from oxygen-lacking gases. The use of a combination of particulates with different impregnates within the web for different applications is also appropriate in certain implementations. For example, it is possible to use of a mixture of two activated carbons.

The presence of water enhances $H_2S$ removal in combination with many of the above specified impregnates. Water can be stored on the carbon surface or within the web through pre-humidification or through the use of impregnates or additional adsorbents that attract water vapor to their surfaces during the application. Several types of adsorbents can be used to cover the desired ranges of humidity and they include molecular sieves, activated alumina, silica gel and activated carbons. These adsorbent can be further modified by oxidation, heating, or impregnation. Impregnation is commonly done with alkali metals sulfate, citric acid, alkali metals carbonates, alkali metals bicarbonates, lithium and sodium chlorides, calcium chloride, and/or a mixture thereof.

It is also possible to add water adsorbent particles that will be capable of picking up water at low humidity or storing it. These water adsorbent particles can release some of their humidity in dry conditions. The presence of the released water can then enhance $H_2S$ removal in dry conditions.

Besides using particles that have been impregnated or coated with reactive species, it should be apparent that these modifications can be performed after forming the fibrous web and structures. Imparting reactive activity to the particles and web after forming the fibrous web and structure can be accomplished using various different coating processes. For example, spray coating, dip coating, aerosol deposition, chemical vapor deposition, and vacuum coating. A final step can involve a drying process that may, or may not, include thermal treatments, gas purging, or vacuum methods.

Furthermore, the chemistry of the walls of the first layer can be made to adsorb acidic, basic, and organic and water vapors, as well as several specific classes of compounds including reactive carbonyl compounds, such as formaldehyde, acetaldehyde and acetone. The reactive materials can be held together with adhesive or fibers to encapsulate, or simply hold, the particles. Also, additional scrim materials can be attached to hold the reactive material in place and minimize shedding of particles. The reactive material can also be sandwiched between layers of scrim. The scrim can help to produce the channels or space between the layers. This can be accomplished with a high loft scrim material that gives the proper spacing as well as ability to hold all the reactive particles in the media.

Additional Functional Layers

It can also be advantageous to provide one or more additional functional layers to the webs besides the nonwoven fine fiber composite webs. A functional layer can be a coating or a separately formed layer of material. For example, microporous layers, foam layers, expanded polytetrafluoroethylene layers, water repellent layers or coatings, odor masking layers or coatings, or a combination thereof may be provided on one or both sides of the nonwoven fine fiber composite webs of the invention.

Such additional layers can add additional functionality to the web when that functionality is not practical to build into the web as it is formed. For example, for providing adhesion of the web onto a substrate, it may be desirable not to provide a fluorochemical coating to the web. But where oil repellency is desirable in the application, fluorochemicals provide the requisite protection.

Experimental Protocols

Deodorizing gas filters were evaluated via two main metrics, (1) hydrogen sulfide ($H_2S$) breakthrough time and (2) pressure drop as a function of airflow. $H_2S$ breakthrough times were used to measure filter life based upon British Standard BS 7127 Part 101 and/or ASTM D5160-95, both of which are gas-phase adsorption tests of activated carbon. Pressure drop testing generally involved testing pressure drop across a media. In conducting the pressure drop test, a 1 square inch piece of media was tested at an airflow of about 500 cc/min and the pressure drop from one side of the media to the other was measured.

Deodorizing Gas Filter Performance

Table 1 below provides $H_2S$ breakthrough times for a filter with activated carbon and fiber matrix constructed in accordance with the concepts described herein, in comparison to a selection of commercially available products. As previously described, it is desirable to have extended $H_2S$ breakthrough time and minimal pressure drop due to airflow.

Comparative Media 1 was an activated carbon with a mean particle size of about 300 micron, ball hardness of 97, less than 20 percent by weight impregnate, web thickness of 1.7 mm and carbon basis weight of 400 gm/m². Comparative Media 2 was obtained from an ostomy pouch sold with product number 411491 by ConvaTec, which has a headquarters location in Princeton, New Jersey. Comparative Media 3 was obtained from a Coloplast ostomy pouch with product number 14357, sold by Coloplast Corp. of Minneapolis, Minnesota. Comparative Media 4 was obtained from an ostomy pouch sold by Hollister Incorporated of Libertyville, Illinois. $H_2S$ tests were conducted on parts without any preconditioning beyond ambient conditions of RH or temperature. The tests were conducted with a 2 ppm $H_2S$ breakthrough time using a $H_2S$ challenge concentration of 25 ppm at an air flow of 500 cc/min. The tests were conducted at 50 percent relative humidity and less than 6 percent relative humidity.

TABLE 1

| Media | Breakthrough time (minutes) at 50 % RH | Breakthrough time (minutes) at less than 6 % RH |
|---|---|---|
| Activated carbon and fiber matrix (NICOM) | 1430 | 330 |
| Comparative Media 1 | 710 | 146 |
| Comparative Media 2 | 880 | 100 |
| Comparative Media 3 | 200 | 70 |
| Comparative Media 4 | 60 | 30 |

As is apparent from Table 1, the activated carbon and fiber matrix of the invention had nearly 50 percent or longer improvements in breakthrough times.

Table 2 provides pressure drop results for the filter media constructed with activated carbon and fiber matrix and the same comparative medias described with reference to Table 1. It is desirable to have a low pressure drop to reduce or eliminate ostomy bag ballooning. Pressure drop was measured (in-wg) at 500 cc/min of air flow.

TABLE 2

| Media | Pressure drop (inches water gauge) |
|---|---|
| Activated carbon and fiber matrix 260 g/m$^2$ | 2 |
| Comparative Media 1 | 1 |
| Comparative Media 2 | 11 |
| Comparative Media 3 | 32 |
| Comparative Media 4 | 5 |

Table 3 presents the construction details of the above mentioned test samples.

TABLE 3

| | | |
|---|---|---|
| activated carbon and fiber matrix 260 g/m$^2$ | Shape | Round |
| | Gas Flow | Axial, (Through Face of Media) |
| | Material | Described in WO 2007/095363 |
| | Inlet | Inside Face of Filter |
| | Outlet | Outside Face of Filter |
| Comparative Media 1 | Shape | Round |
| | Gas Flow | Laterally through media |
| | Material | Carbon with Binder between two Scrims |
| | Inlet | Outside Perimeter |
| | Outlet | Center |
| Comparative Media 2 | Shape | Round |
| | Gas Flow | Laterally through media |
| | Material | Carbon on foam |
| | Inlet | Outside Perimeter |
| | Outlet | Center |
| Comparative Media 3 | Shape | Crescent |
| | Gas Flow | Laterally through media |
| | Material | Carbon on Foam |
| | Inlet | Right End |
| | Outlet | Left End |
| Comparative Media 4 | Shape | Crescent |
| | Gas Flow | Laterally through media |
| | Material | Carbon and Felt |
| | Inlet | Perimeter |
| | Outlet | Outside Face |

Example 1: Creation of Activated Carbon and Fiber Matrix

A nonwoven fine fiber composite web made in accordance with the description herein was produced using carbon particles impregnated with potassium iodine and potassium carbonate and elastomeric polyurethane. The polyurethane was obtained from Lubrizol Corporation (of Cleveland, OH) as was identified as SP-80A-150 and a lot #CD7NRAZ7Z.

The polyurethane elastomer was dissolved in ethyl alcohol at 60° C. by vigorous stirring for 5-6 hours until the solids were completely dissolved, followed by cooling to 25° C. overnight. The solids content of the solution was 13.5% by weight and the viscosity of the resulting solution was around 200 cP as measured using a Brookfield viscometer. This polymer solution was electrospun. During the electrospinning, carbon powder (209C Kina carbon, 80×200 mesh size, available from Calgon Carbon Corporation of Columbus, OH) was constantly weighed and fed at a steady feed rate into the flow of polymer solution using a volumetric screw feeder with an auger. The flow rate was metered to provide about 130 g/m$^2$ of carbon powder into the finished composite web. The particles were then fed into a deflocculator, which imparted sufficient momentum to the particles enabling them to deposit onto the collector. This was accomplished using compressed air at the deflocculator. In this manner, the particles and fibers were deposited simultaneously, creating an intermixed composite. A total of 130 g/m$^2$ of carbon powder were incorporated inside the fine fiber composite and the polyurethane fibers weighed about 7 g/m$^2$.

Example 2: Creation of Activated Carbon and Fiber Matrix with Intermediate Carbon Loading Levels In the same manner as described in Example 1, another nonwoven fine fiber composite web was generated using the same fine fiber materials and particles, but with a higher particle loading rate. A total of 260 g/m$^2$ of carbon powder were incorporated inside the fine fiber composite and the polyurethane fibers weighed about 14 g/m$^2$.

Example 3: Creation of Activated Carbon and Fiber Matrix with Higher Carbon Loading Levels In the same manner as described in Example 1, another nonwoven fine fiber composite web was generated using the same fine fiber materials and particles. A total of 390 g/m$^2$ of carbon powder were incorporated inside the fine fiber composite and the polyurethane fibers weighed about 21 g/m$^2$.

Example 4

The sample generated in Example 2 was calendared to the extent that a thickness reduction of 33 percent was achieved in the sample. The calendaring was achieved by pressing the fine fiber composite matrix between a roller and a hard surface to reduce thickness.

Figure 14:
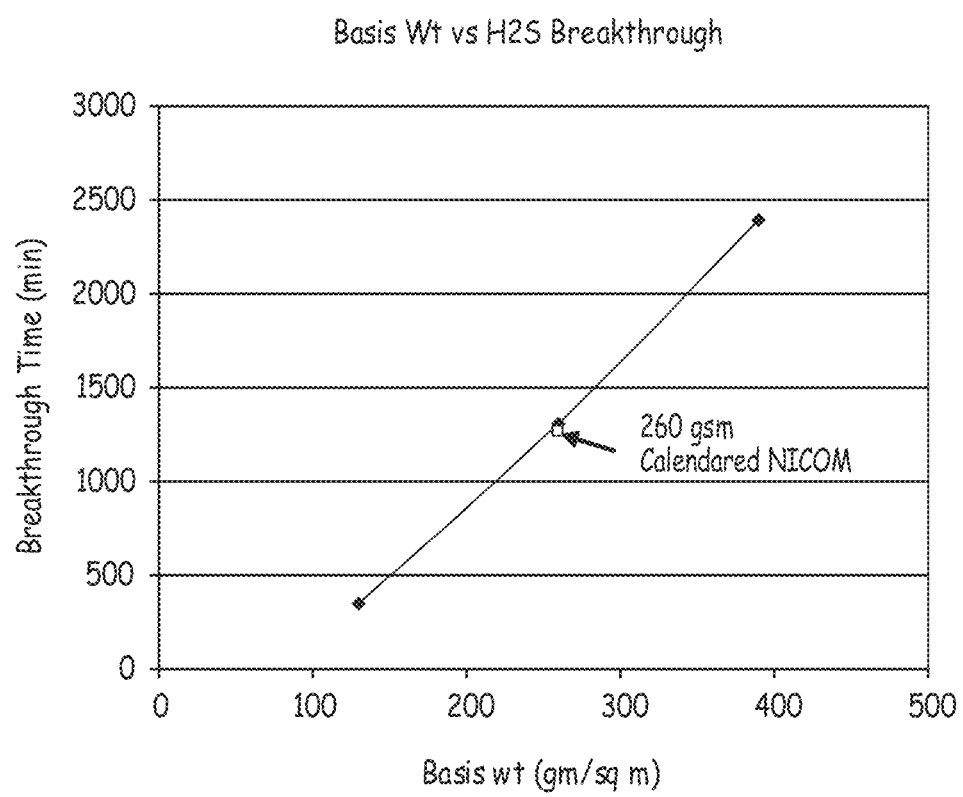
FIG. 14 is a chart depicting basis weight versus $H_2S$ breakthrough for various media constructions.

H$_2$S breakthrough performance of Examples 1-4 above are shown in FIG. 14. As is shown in FIG. 14, the influence of basis weight on H$_2$S performance is demonstrated, showing an increase in breakthrough performance observed with increasing basis weight of fine fiber composite matrices. Further, as is observed at the 260 gm/m$^2$ fine fiber composite matrices, there was no observed lack of influence on H$_2$S performance from calendaring.

Figure 15:
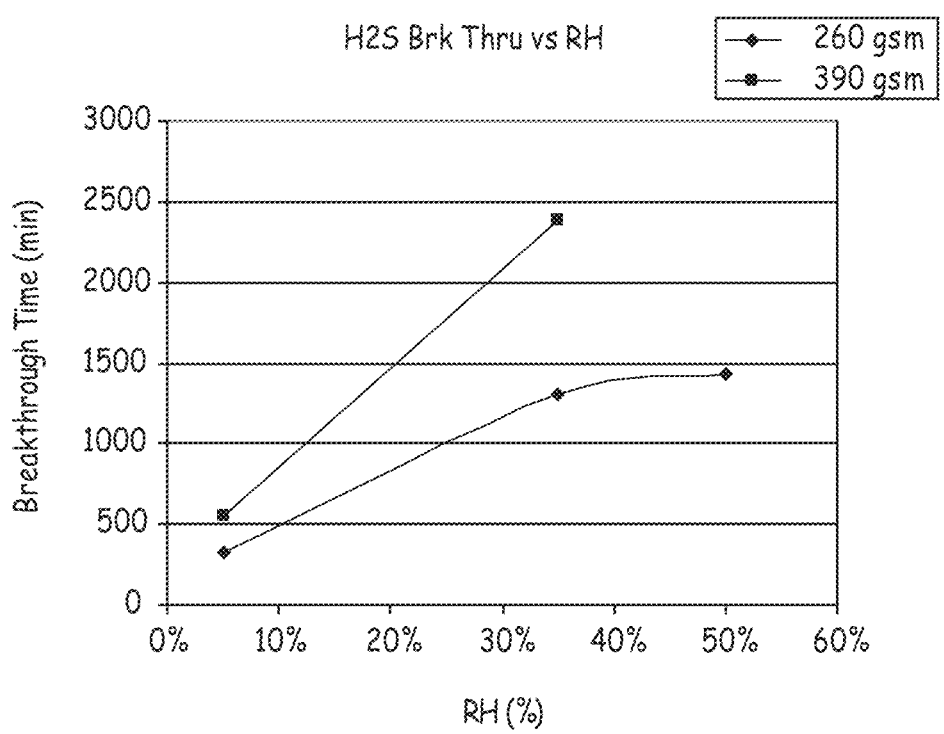
FIG. 15 is a chart showing $H_2S$ breakthrough as a function of relative humidity.

FIG. 15 demonstrates the influence of test gas relative humidity on two basis weights of activated carbon and fiber matrix. As is apparent from FIG. 15, the breakthrough time increased with both materials as relative humidity increased. Examples of Absorbent Breather Filters Utilizing Activated Carbon and Fiber Matrix All of the samples generated in the Examples 1-4 were assembled into axial designs as shown in FIGS. 4-8, and samples were tested according to the experimental protocols described earlier.

Example 10

Use of impregnated adsorbent improved the efficiency and capacity of the media for H$_2$S.

Table 4 below shows a comparison between activated carbon and fiber matrix media compared to a non impregnated activated carbon based media. Airflow was set at 500 cc/min using an H$_2$S challenge concentration at 25 ppm H$_2$S and 35 percent relative humidity. The breakthrough time was measured at the point the concentration of $H_2S$ reached 2 ppm

TABLE 4

| Media | Breakthrough time (minutes) |
|---|---|
| activated carbon and fiber matrix 130 g/m² | 260 |
| Non impregnated media | 5 |

Example 11

Figure 16:
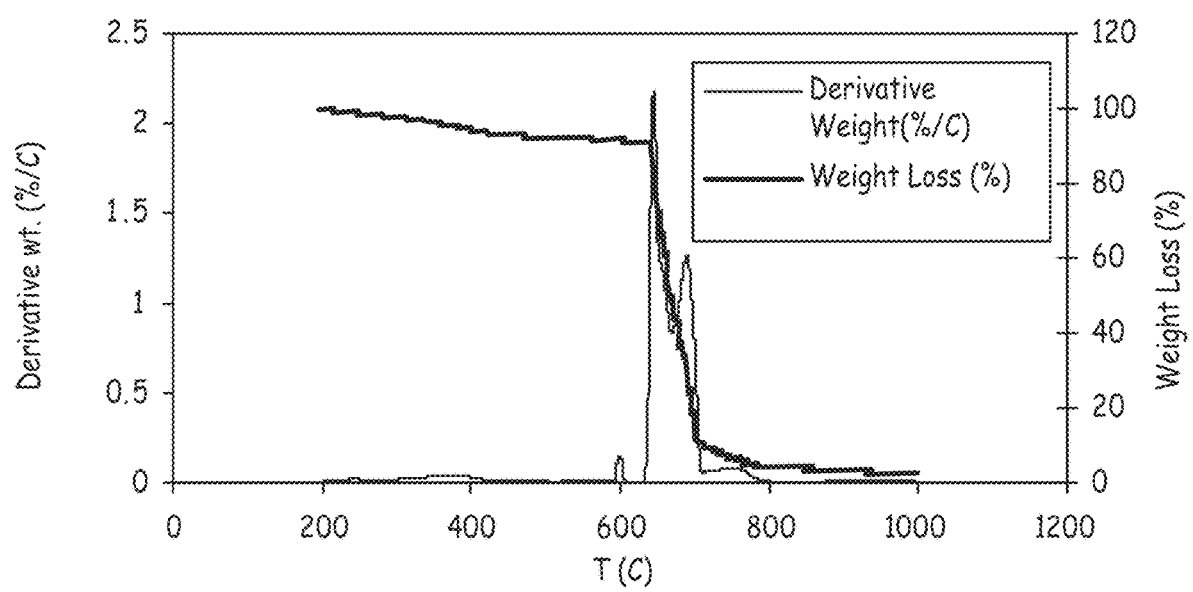
FIG. 16 is a thermal analysis of activated carbon and fiber matrix media.

Activated carbon and fiber matrix media contain various proportions of activated carbon. FIG. 16 shows the thermal analysis of activated carbon and fiber matrix media. The sample was heated to 600° C. in N2 atmosphere at a rate of 10° C./min then maintained at an isothermal for 30 minutes followed by heating in air to 1000° C. at 10° C./min. Analysis of the data shows that 90 percent of the tested activated carbon and fiber matrix media is composed of activated carbon while 7 percent of the weight is web based and the rest are ash and inorganic residue.

Example 12

The web in activated carbon and fiber matrix media does not block the pores and the surface area of the particles. The porous structure as well as the surface area of the activated carbon and fiber matrix media in Example 12 was measured using nitrogen adsorption isotherms. The structural parameters of the activated carbon and fiber matrix material were compared to those of the constituent activated carbon.

The structural parameters are summarized in Table 5 below. Pore volumes were calculated using density functional theory while the surface area was calculated using Brunauer-Emmett-Teller (BET) theory. The BET surface area of the activated carbon and fiber matrix media and the activated carbon are similar if we take into consideration that activated carbon and fiber matrix media evaluated in Example 12, is composed of 90% wt of carbon.

TABLE 5

| | $S_{BET}$ (m2/g) | S mic (m2/g) | (Å) | V < 10Å | V < 20Å | Vt | Vmic/Vt |
|---|---|---|---|---|---|---|---|
| activated carbon | 1002 | 785 | 19.0 | 0.219 | 0.36 | 0.383 | 0.928 |
| activated carbon and fiber matrix | 906 | 703 | 19.2 | 0.184 | 0.31 | 0.341 | 0.909 |

A variety of benefits are realized through the use of activated carbon and fiber matrix-based adsorbent breather filter for use with an ostomy bag. This configuration provides a structure that allows the use of carbon particles less than 150 micron in one dimension. The small carbon particle size provides greater exposure of the activated carbon to the contaminant intended to be adsorbed, which produces a higher efficiency filter per given volume. Furthermore, the small amount of fine fiber used as a binder allows for a larger percentage of the utilized space to be occupied by adsorbent allowing for near optimal capacity. Binders utilized in standard carbon filter construction can block 30 to 50 percent of the activated carbon adsorption sites. An activated carbon and fiber matrix does not require use of a binder. It consists of fine fiber and carbon only allowing it to maintain a very high utilization of the activated carbon. Higher utilization results in better efficiency and capacity per unit volume. In one embodiment, the adsorbent layer is substantially free of any binder. For example, the adsorbent layer can contain 2% or less binder material by weight.

These benefits allow further efficiency and capacity improvements. For example, a filter constructed in this fashion has a lower space requirement and hence can lead to reduced product size and cost. In addition, axial flow through thin filter layers can result in minimizing pressure drop. The simplified filter construction can eliminate extra film layers meant to promote radial flow. Furthermore, a wide variety of filter profiles such as round, crescent, rectangular, etc. can be accomplished.

The low pressure drop and high efficiency allow the filter to be constructed with airflow through the face of the filter media which also allows an expanded polytetrafluoroethylene (ePTFE) filter media to be added to the top (outer or inlet), and if desired, to the bottom (bag or exit), side of the filter. The value of this construction is that the ePTFE can be added without the extra penalty of pressure drop due to a small filter area that a radial flow design would create. Moreover, the flexibility and thin profile of the activated carbon and fiber matrix based filter will allow the ostomy product to conform more closely to the patient's body.

Example 13

As a further analysis to support Example 12, a $H_2S$ breakthrough comparison of media made in accordance with the present invention was performed to analyze any negative influence of the fine fibers. This test analyzed the $H_2S$ performance of a 22 mm diameter 390 g/m² activated carbon-containing the fine fiber web described by this invention in comparison with a loose fill constructed to the same dimensions and using an equivalent amount of the same activated carbon. The results in Table 6 demonstrate that there was no improvement in the part without the fine fiber. The loose fill part $H_2S$ time was lower than the 390 g/m² activated carbon-containing fine fiber. This was most likely due to some test variability and the fact that the carbon was not as evenly distributed, that is, the activated carbon-containing fine fiber construction allows for more consistent layering of the carbon which is critical for a thin filter.

TABLE 6

| Sample | $H_2S$ Breakthrough (min) |
|---|---|
| 390 g/m² activated carbon-containing fine fiber media | 2370 |
| Loose fill activated carbon | 1770 |

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the present specification. The claims are intended to cover such modifications and devices.

The above specification provides a complete description of the structure and use of the invention. Since many of the embodiments of the invention can be made without parting from the spirit and scope of the invention, the invention resides in the claims.

What is claimed is:

1. A filter assembly for an enclosure, comprising:
an enclosure side and a side opposite from the enclosure side;
a first layer which is gas permeable; and
an adsorbent layer comprising adsorbent particles;
wherein the enclosure side of the filter assembly comprises:
an adhesive zone in which adhesive is present having an outer adhesive perimeter;
a weld area adjacent to at least a portion of the adhesive zone, where the filter assembly is heat-sealable to the enclosure at the weld area.

2. The filter assembly of claim 1, wherein the weld area completely surrounds the adhesive zone.

3. The filter assembly of claim 1, wherein the weld area is adjacent to the adhesive zone along the outer adhesive perimeter.

4. The filter assembly of claim 1, wherein the weld area does not overlap the adhesive zone.

5. The filter assembly of claim 1, wherein the weld area partially overlaps the adhesive zone.

6. The filter assembly of claim 1, wherein the adhesive zone overlaps an outer perimeter of the adsorbent layer.

7. The filter assembly of claim 1, wherein the adsorbent layer comprises activated carbon and is substantially free of binder material.

8. The filter assembly of claim 1, wherein the adsorbent layer contains less than 2% binder material by weight.

9. The filter assembly of claim 1, wherein the adsorbent layer comprises the adsorbent particles dispersed in a fine fiber web.

10. The filter assembly of claim 1, wherein the adsorbent layer further comprises a fine fiber web comprising electrospun polymeric fine fibers.

11. The filter assembly of claim 1, wherein the adsorbent layer comprises a matrix of the fine fibers and comprises activated carbon.

12. The filter assembly of claim 11, wherein the adsorbent layer comprises about 1 to 30 weight percent fine fiber having a fiber diameter of about 0.001 to 5 micron and 70 to 99 weight percent adsorbent particles.

13. The filter assembly of claim 1, wherein the adsorbent layer comprises carbon and has a carbon basis weight of 130 $g/m^2$ or higher.

14. The filter assembly of claim 1, wherein the adsorbent layer comprises carbon and has a carbon basis weight of 260 $g/m^2$ or higher.

15. The filter assembly of claim 1, where the first layer comprises a laminate of expanded PTFE and a scrim layer.

16. The filter assembly of claim 1, further comprising a second layer that is gas permeable, wherein the adsorbent layer is sandwiched between the first layer and the second layer, wherein the second layer is liquid impermeable.

17. An ostomy filter and an ostomy bag comprising:
an ostomy bag defining a stoma opening and a vent opening; and
an ostomy filter attached to the ostomy bag to cover the vent opening, the ostomy filter comprising:
a bag side and a side opposite from the bag side, wherein the bag side of the ostomy filter is secured to the ostomy bag;
a first layer which is gas permeable and liquid impermeable; and
an adsorbent layer of adsorbent particles;
wherein the bag side of the ostomy filter comprises:
an adhesive zone in which adhesive is present, the adhesive zone having an outer adhesive perimeter and an inner adhesive perimeter, wherein the inner adhesive perimeter surrounds an exit opening, wherein the adhesive attaches the ostomy filter and the ostomy bag at the adhesive zone; and
a weld area adjacent to at least a portion of the adhesive zone, where the filter assembly is heat-sealable to the ostomy bag at the weld area, wherein the ostomy filter is attached by heat seal to the ostomy bag at the weld area.

18. The filter assembly of claim 17, wherein the adsorbent layer comprises carbon and has a carbon basis weight of 130 $g/m^2$ or higher.

19. The filter assembly of claim 17, wherein the ostomy bag is a flexible bag comprising plastic.

20. A system of filter assemblies for an enclosure and a release liner, comprising:
a release liner; and
a plurality of filter assemblies located on the release liner, each filter assembly comprising:
an enclosure side and a side opposite from the enclosure side;
a first layer which is gas permeable; and
an adsorbent layer comprising adsorbent particles;
wherein the enclosure side of the filter assembly comprises:
an adhesive zone in which adhesive is present having an outer adhesive perimeter;
a weld area adjacent to at least a portion of the adhesive zone, where the filter assembly is heat-sealable to the ostomy bag at the weld area.

* * * * *